United States Patent [19]

Neuenhofer et al.

[11] Patent Number: 6,010,868
[45] Date of Patent: Jan. 4, 2000

[54] METHOD FOR STABILIZING HYDROLYSIS-SENSITIVE MOLECULES OR MOLECULAR MOIETIES

[75] Inventors: Stephan Neuenhofer; Reinhard Käsmarker, both of Marburg; Götz Walter, Grosseelheim; Hans-Peter Harthus; Günther Nau, both of Marburg; Heinz-Jürgen Skrzipczyk, Neu-Isenburg; Peter Molz, Mainz; Norbert Madry, Marburg, all of Germany

[73] Assignee: Behring Diagnostics GmbH, Marburg, Germany

[21] Appl. No.: 08/750,743

[22] PCT Filed: Jun. 23, 1995

[86] PCT No.: PCT/EP95/02446

§ 371 Date: Dec. 20, 1996

§ 102(e) Date: Dec. 20, 1996

[87] PCT Pub. No.: WO96/00284

PCT Pub. Date: Jan. 4, 1996

[30] Foreign Application Priority Data

Jun. 24, 1994 [DE] Germany .............................. 44 21 907
Mar. 31, 1995 [DE] Germany .............................. 195 11 940

[51] Int. Cl.[7] .................................................. G01N 33/53
[52] U.S. Cl. .............................. 435/7.9; 435/28; 435/963; 435/975
[58] Field of Search .............................. 435/7.9, 28, 7.72, 435/963, 975; 436/540, 546–548

[56] References Cited

U.S. PATENT DOCUMENTS

| 4,645,646 | 2/1987 | Gadow et al. . |
| 4,657,873 | 4/1987 | Gadow et al. . |
| 5,302,533 | 4/1994 | Kricka . |
| 5,445,936 | 8/1995 | Piran et al. .................................. 435/6 |

FOREIGN PATENT DOCUMENTS

| 0 073 593 | 3/1983 | European Pat. Off. . |
| 0 135 071 | 3/1985 | European Pat. Off. . |
| 0 257 541 | 3/1988 | European Pat. Off. . |
| 0 330 050 | 8/1989 | European Pat. Off. . |
| 0 442 372 | 8/1991 | European Pat. Off. . |
| 0 487 301 | 5/1992 | European Pat. Off. . |
| WO 93/20074 | 10/1993 | WIPO . |

OTHER PUBLICATIONS

Law et al., J. Biolum. & Chemilum., 4:88–98, Jan. 1989.
Nargessi et al., "Use of Antibodies Against the Label in Non–separation Non–isotopic Immunoassay: 'Indirect Quenching'Fluoroimmunoassay of Proteins," *Chemical Abstracts*, Abstract No. 71265, vol. 91, (Aug. 27, 1979).

*Primary Examiner*—Christina Y. Chan
*Assistant Examiner*—Patrick J. Nolan
*Attorney, Agent, or Firm*—Finnegan, Henderson, Farabow, Garrett & Dunner, L.L.P.

[57] ABSTRACT

The invention concerns a method of stabilizing molecules, or parts of molecules, which are sensitive to hydrolysis, in particular hydrolysis-sensitive labels or label-containing tracers in aqueous solutions. The invention also concerns kits for carrying out immunological assays making use of the method proposed.

17 Claims, 5 Drawing Sheets

METHOD FOR STABILIZING HYDROLYSIS-SENSITIVE MOLECULES OR MOLECULAR MOIETIES

The present invention relates to a method for stabilizing hydrolysis-sensitive molecules or molecular moieties. The invention particularly relates to a method for stabilizing hydrolysis-sensitive labels and label-containing tracers in aqueous solutions.

Immunological detection methods have become very important in in vitro diagnosis. The reason for this is that they are highly specific and extremely sensitive. In addition, these methods are distinguished by simple manipulation. The detection methods are based on the immunological interaction between the analyte to be detected and its binding partner or binding partners.

In the case of sandwich assays, the analyte is bound by two different antibodies in sandwich fashion. One of the two antibodies carries a label by which means its concentration, and thus that of the sandwich complex, can be determined. The sandwich method cannot be applied to small analytes because two different antibodies cannot bind simultaneously to the analyte for steric reasons. Competitive assays are used in such cases as a rule. In these, the analyte and a synthetic derivative of the analyte compete for the binding sites on the antibody. As a rule, either the analyte derivative (classical competitive method) or the antibody is labeled.

Conventional labels are, for example, radioactive isotopes or luminescent (fluorescent, phosphorescent, chemiluminescent, bioluminescent etc.) substances or substances capable of absorption. The labeled reagent (antibody, analyte derivative) is referred to as tracer hereinafter.

The tracer is frequently stored in an aqueous solution ready for use. Since the labels are in many cases substances not resistant to hydrolysis, the storage in aqueous solution means, as a rule, an unintended limitation of the stability. This is manifested in particular by the height of the measured signal decreasing with increasing storage time. As a consequence, the shelf life of the complete kit is often reduced.

The present invention was thus based on the technical problem of finding a method which reduces the sensitivity to hydrolysis of molecules, molecular moieties and, in particular, substances used as labels in immunological detection methods.

This technical problem is solved by providing the embodiments defined in the claims. It has been found, surprisingly, that addition of antibodies directed against the molecules, molecular moieties or labels to be stabilized considerably reduces the sensitivity of said substances to hydrolysis. The hydrolysis-protective effect presumably derives from the fact that the attack of hydrophilic particles ($H_2O$, $OH^-$, $H_3O^+$) is hindered for steric reasons and/or by creation of a hydrophobic environment. A hydrolysis-protective effect of this type thus extends in principle to all hydrolysis-sensitive molecules, molecular moieties or labels provided that antibodies against these substances can be produced in order to be able to carry out the method according to the invention.

The invention thus relates to a method for stabilizing hydrolysis-sensitive molecules or molecular moieties in aqueous solution, which comprises adding to the aqueous molecule or molecular moiety solution antibodies directed against the molecules or molecular moieties. The term "stabilization" means in connection with the present invention that the hydrolysis of a molecule, molecular moiety or label is prevented or slowed down. The term "molecule" means a particle which is held together by chemical bonds and which comprises two or more atoms of the same type or different types. This designation also covers in connection with the present invention ions or radicals of the molecules. The term "molecular moiety" means parts of this molecule which can be produced by elimination from the complete molecule. The term "hydrolysis-sensitive" designates in connection with the present invention the ability of a compound, in this case a molecule, molecular moiety, a label or tracer, to undergo a chemical reaction involving $H_2O$ and/or $H_3O^+$ and/or $OH^-$, which leads to a product which is unwanted, i.e. no longer able to produce a signal or with limited ability to produce a signal.

The term "antibody" means monoclonal or polyclonal antibodies. In connection with the present invention, this term also covers chimeric antibodies, bispecific antibodies, antibody fragments (for example (Fab'$_2$), Fab, Fv), (semi) synthetic and chemically modified antibodies or antibody fragments.

The method according to the invention makes it possible considerably to increase the stability in aqueous solution of hydrolysis-sensitive molecules or molecular moieties against which antibodies can be directed.

The invention relates in particular to a method for stabilizing labels used in immunological detection methods. The term "label" means in connection with the present invention a label, a marker or a signal emitter in molecular form. This label can be a group capable of luminescence, fluorescence, phosphorescence, chemiluminescence, bioluminescence or electroluminescence. A label is, in particular, an acridinium ester, an acridiniumacylsulfonamide, a luminol or derivatives thereof, an isoluminol or derivatives thereof, a dioxetane, a luciferin, an oxalic ester or an oxalic acid amide. The method according to the invention thus makes it possible considerably to increase the stability of tracers which have a label and which can be used, for example, in detection methods, in particular in immunological detection methods.

The invention additionally relates to a kit comprising a hydrolysis-sensitive molecule or a hydrolysis-sensitive molecular moiety and a stabilizing antibody directed against it. The invention particularly relates to a kit wherein the molecular moiety to be stabilized is a label or the molecule to be stabilized is a tracer. The kit according to the invention can preferably be used in an immunological detection method. In a particularly preferred embodiment, the invention relates to a kit for carrying out a competitive immunological detection method, comprising an analyte derivative and an antibody, wherein either the analyte derivative or the antibody has a label, and an antibody directed against the label. In another particularly preferred embodiment, the invention relates to a kit for carrying out a sandwich assay, comprising two antibodies which are directed against the analyte and which bind to different epitopes of the analyte and wherein one of the antibodies has a label, and an antibody directed against the label.

The antibodies directed against the analyte may be of polyclonal, monoclonal, chimeric, synthetic or semisynthetic origin. Finally, the invention relates to a kit as defined above, wherein the antibody directed against the molecule, the molecular moiety or the label is a monoclonal antibody, a polyclonal antibody, a chimeric antibody, a synthetic or semisynthetic antibody, an antibody fragment, a chemically modified antibody or a chemically modified antibody fragment.

The following examples illustrate the invention.

EXAMPLE 1

Stabilization of an Anti-PSA Tracer

Step 1: Preparation of a Monoclonal Antibody Against a Luminogenic Acridiniumacylsulfonamide Label To prepare monoclonal antibodies, BALB/c mice received subcutaneous or intraperitoneal injections of 10 µg of acridiniumacylsulfonamide-BSA which was emulsified in complete Freund's adjuvant. These were followed by 4 to 5 additional immunizations without adjuvant (at intervals of four weeks in each case). The mice underwent intravenous reimmunization on the last four days before the fusion (10 µg per day).

To prepare hybridomas, the immunized animals were sacrificed by cervical luxation. The spleen was removed under aseptic conditions and teased apart in order to obtain a single-cell suspension of spleen cells in serum-free Dulbecco's modified Eagle Medium (DMEM). The cells were collected by centrifugation (5 min; 1800 rpm) and washed once in DMEM. The total number of cells was determined by hemocytometer counting using the trypanblue exclusion technique. The mouse myeloma cells (Sp2/0) used as fusion partners were washed twice in serum-free DMEM, and collected by centrifugation (10 min, 1000 rpm) and counted as described above for the spleen cells.

About $10^8$ spleen cells were mixed with $2 \times 10^7$ Sp2/0 mouse myeloma cells. After centrifugation at 1000 rpm for 10 minutes, the supernatant was removed, and 1 ml of polyethylene glycol (PEG 4000, Merck, 50%) was added to the pellet in the vessel. The pellet was then resuspended by gently tapping and incubated at 37° C. for 1 minute. 10 ml of serum-free DMEM were added dropwise while tapping gently, and the mixture was incubated for 2 to 4 minutes. The fused cells were subsequently centrifuged at 1000 rpm for 10 minutes. The resulting cell pellet was suspended in 20% fetal calf serum (FCS) and HAT (hypoxanthine 0.1 mM; aminopterin 0.4 µM; thymidine 16 µM)-containing DMEM and plated out on culture plates (Nunc) with 24 wells with a concentration of approximately $5 \times 10 - 10^6$ cells per well. After 2 to 3 weeks, single cell colonies were removed from the individual wells and cultivated in the wells of a new culture plate.

The culture supernatants were screened for antigen-specific antibodies by the EIA technique. Each well coated with acridinium-BSA (3 µg/ml) in a microtiter plate was charged with 100 µl of the supernatant and incubated at room temperature for 1 hour. After washing, 100 µl of a rabbit-anti-mouse antibody-POD conjugate was added for an additional hour at room temperature. After incubation with the substrate for 30 minutes, the color development was read off at 492 nm in a Behring-ELISA-processor (BEP). Hybridomas which produce antibodies with a suitable antigenic specificity were selected and cloned using a single-cell manipulator. To prepare large amounts of monoclonal antibodies, the clones were grown in mass culture. The subsequent purification of the individual monoclonal antibodies was carried out by protein A chromatography.

Step 2: Preparation of an Anti-PSA Tracer 0.1 mg of an anti-PSA MAb (monoclonal antibody directed against prostate-specific antigen (PSA); for example BW 92-284/03, Behringwerke AG) was dissolved in 0.7 ml of 0.1 molar phosphate buffer (pH 8.0). To this solution were added 30 µl of a labeling solution (0.1 mg of acridiniumacylsulfonamide (with N-succinimidyl reactive group) per ml of acetonitrile), and the reaction solution was incubated at room temperature for 15 minutes. Subsequently, 0.3 ml of an aqueous lysine solution (10 mg/ml) was added, and incubation was continued for 15 minutes. The tracer was purified by gel chromatography (Sephadex G 25).

The purified tracer was finally dissolved at a concentration of 600 ng/ml in 0.05 M of tris/HCl buffer (pH 7.4; 2 g of bovine serum albumin, 8.8 g of NaCl and 0.5 g of sodium azide per liter).

Step 3: Stabilization of the Tracer Solution

Tracer solution A: for stabilization, anti-label antibodies (BW 90-9/016, obtained in Step 1, DSM ACC 2183) were added in a concentration of 1 µ/ml to the tracer solution (Step 2).

Tracer solution B: no anti-label antibody was added to the comparison solution.

Result

Figure 1:
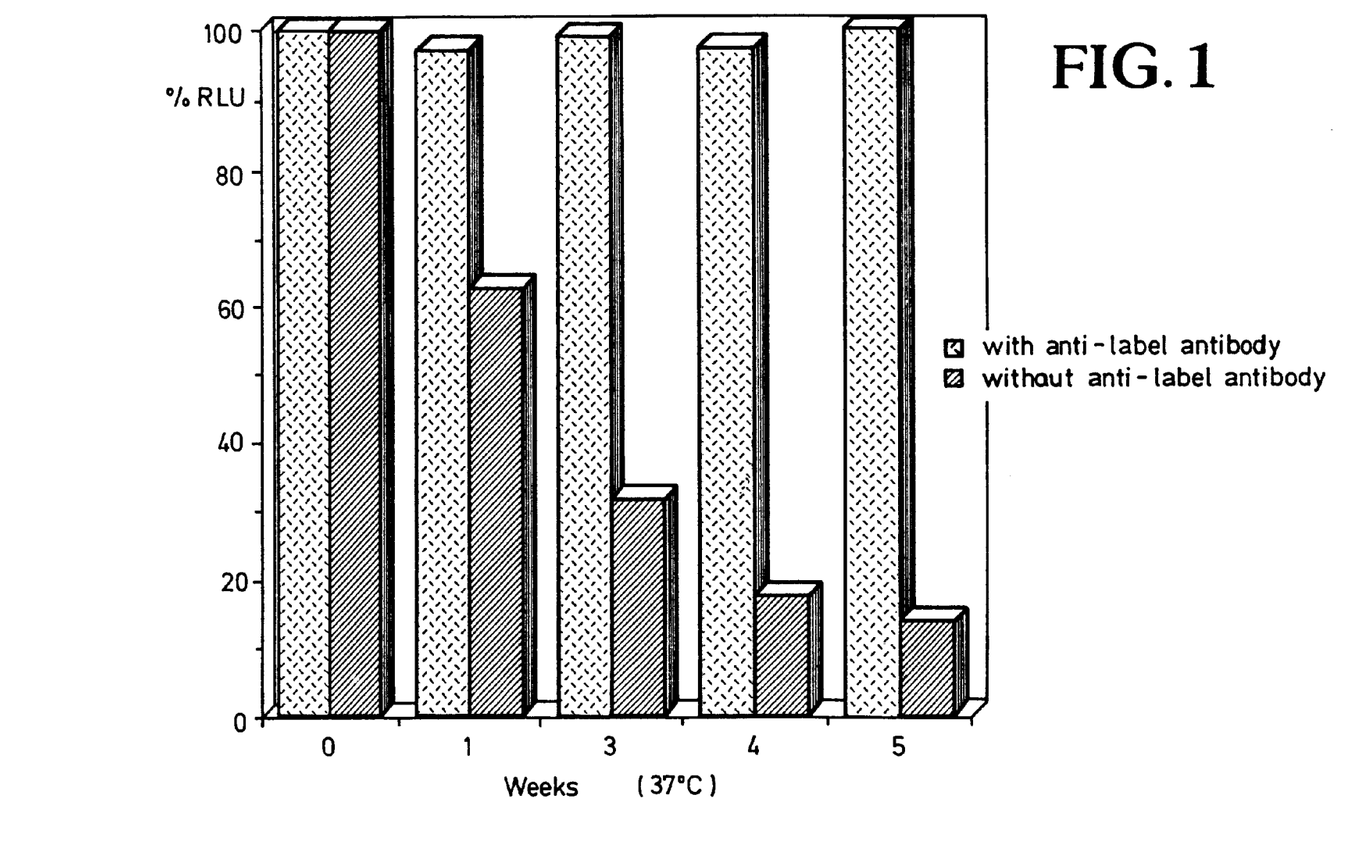
FIG. 1: Signal stability of the anti-PSA tracer after storage at 37° C.; with and without addition of anti-label antibodies; RLU means relative light units.

After storage of tracer solution A and B at 37° C. for five weeks, the initial signal activity was virtually unchanged in the case of tracer solution A and had fallen by 87% in the case of tracer solution B (FIG. 1).

EXAMPLE 2

Stabilization of an anti-T3 tracer

Step 1: Preparation of a Monoclonal Antibody Against a Luminogenic Acridiniumacylsulfonamide Label (EP-A-0 257 541 and EP-A-0 330 050)

The monoclonal antibody was prepared by the method explained in Step 1 of Example 1.

Step 2: Preparation of an Anti-T3 Tracer 0.1 mg of anti-T3 MAb, a monoclonal antibody directed against the thyroid hormone triiodothyronine (T3) (ImmunoGen International Ltd., Order No. 13-3 D8-38, Gateshead, UK) was dissolved in 0.7 ml of 0.1 molar phosphate buffer (pH 8.0). To this solution were added 5 µl of a labeling solution (1.0 mg of acridiniumacylsulfonamide (with N-succinimidyl reactive group) per ml of acetonitrile) by pipette, and the reaction solution was incubated at room temperature for 15 minutes. Subsequently, 0.3 ml of an aqueous lysine solution (10 mg/ml) was added and incubation was continued for 15 minutes. The tracer was purified by gel chromatography (Sephadex G 25).

Step 3: Preparation of the Tracer Solution

The purified tracer (Step 2) was dissolved at a concentration of 90 ng/ml in a 0.05 M tris/HCl buffer (pH 7.4; 2 g of bovine serum albumin, 8.8 g of NaCl, 0.25 g of ANS (8-anilinonaphthalene-1-sulfonic acid) and 0.5 g of sodium azide per liter).

Step 4: Stabilization of the Tracer Solution

Tracer solution A: for stabilization, anti-label antibodies (BW 90-9/016, DSM ACC 2183, Step 1) were added at a concentration of 1 µg/ml to the tracer solution (Step 3).

Tracer solution B: no anti-label antibody was added to the comparison solution.

Result

Figure 2:
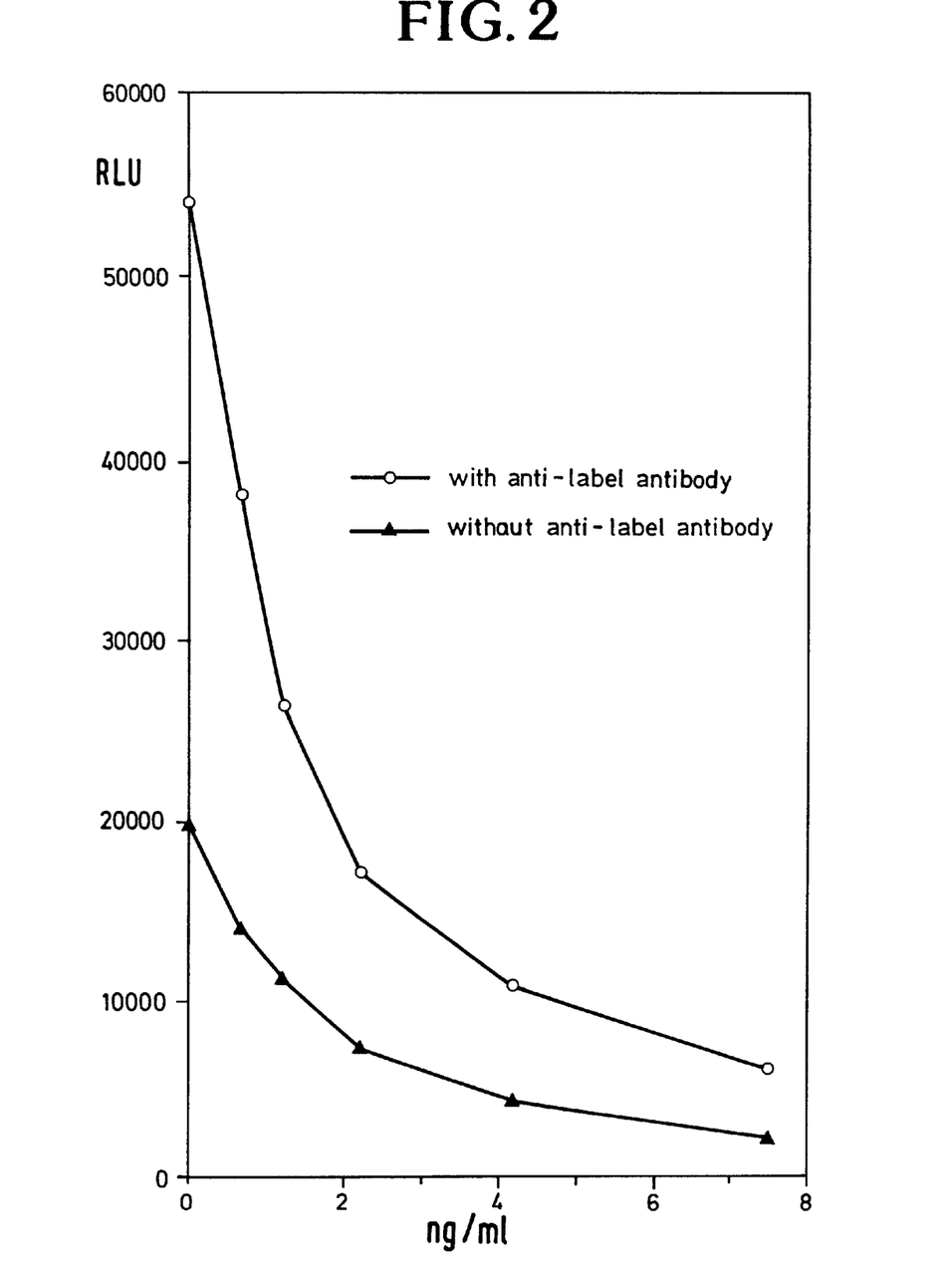
FIG. 2: T3 SPALT (solid phase antigen luminescence technique) assays, carried out with tracers stored at 37° C. for 4 weeks. The SPALT assay is a competitive luminescence immunoassay in which a labeled analyte derivative (=analyte tracer) competes with the analyte to be determined for the binding sites on a labeled antibody (antibody tracer).

FIG. 2 shows the standard plots obtained with the two tracers after storage at 37° C. for four weeks. The height of the signal is distinctly greater for tracer solution A than for tracer solution B.

EXAMPLE 3

Stabilization of a T3 Tracer

Step 1: Preparation of a Monoclonal Antibody Against a Luminogenic Acridiniumsulfonamide Label (EP-A-0 257 541 and EP-A-0 330 050)

The monoclonal antibody was prepared by the method explained in Step 1 of Example 1.

Step 2: Preparation of a T3 tracer 40 mg of rabbit-IgG were dissolved in 8 ml of PBS buffer, pH 7.2. 8 ml of 0.2 M LiBO$_3$ solution (water with 20% of dioxane) and 0.22 ml of GMBS solution (10 mg of N-succinimidyl gamma-maleimidobutanoate/ml dioxane) were added. After 1 hour at room temperature salts were removed via a Biogel P2 column. The resulting eluate ("solution 1") had a volume of about 20 ml.

6.9 mg of triiodothyronine (T3) were dissolved in 0.69 ml of DMSO. 10 μl of N-ethylmorpholine and 2.1 mg of SAMSA (S-acetylmercaptosuccinic anhydride) dissolved in 0.1 ml of DMSO were added. After 30 minutes, 0.1 ml of 1 M aqueous hydroxylamine solution was added by pipette. The solution ("solution 2") was incubated at room temperature for 15 minutes. Solution 1 and solution 2 were mixed and 3 ml of DMSO were added. After 2 hours, salts were removed using Biogel P6, and the conjugate was lyophilized.

0.1 mg of the IgG-T3 conjugate was dissolved in 0.7 ml of 0.1 molar phosphate buffer (pH 8.0). To this solution were added 10 μl of a labeling solution (0.1 mg of acridiniumacylsulfonamide (with N-succinimidyl reactive group) per ml of acetonitrile) by pipette, and the reaction solution was incubated at room temperature for 15 minutes. Subsequently, 0.3 ml of an aqueous lysine solution (10 mg/ml) was added, and incubation was continued for 15 minutes. The tracer was purified by gel chromatography (Sephadex G 25).

Step 3: Preparation of the Tracer Solution

The purified tracer (Step 2) was dissolved at a concentration of 30 ng/ml in a 0.05 M tris/HCl buffer (pH 7.4; 2 g of bovine serum albumin, 8.8 g of NaCl, 0.25 g of ANS and 0.5 g of sodium azide per liter).

Step 4: Stabilization of the Tracer Solution

Tracer solution A: for stabilization, anti-label antibodies (BW 90-9/016, DSM AACC 2183, Step 1) were added at a concentration of 1 μg/ml to the tracer solution (Step 3).

Tracer solution B: no anti-label antibody was added to the comparison solution.

Result

Figure 3:
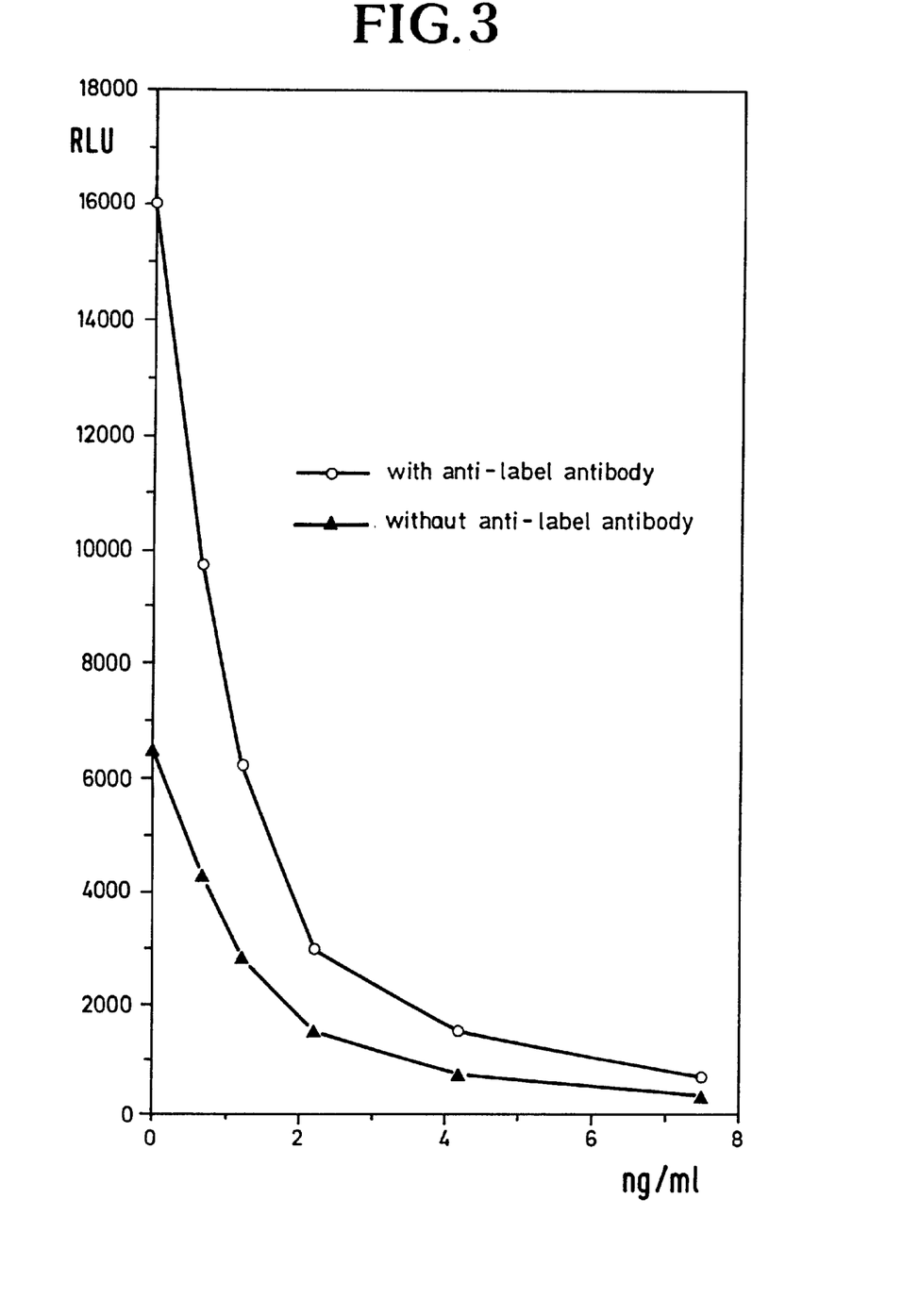
FIG. 3: T3 LIAs (luminescence immunoassay), carried out with tracers stored at 37° C. for 4 weeks. The LIA is a competitive luminescence immunoassay in which a labeled analyte derivative (=analyte tracer) competes with the analyte to be determined for the binding sites on an antibody (which is bound to a solid phase in this case).

FIG. 3 shows standard plots obtained with the two tracers after storage at 37° C. for four weeks. The height of the signal is distinctly greater for tracer solution A than for tracer solution B.

EXAMPLE 4

Comparison of Various Anti-Label Antibodies

Figure 4A:
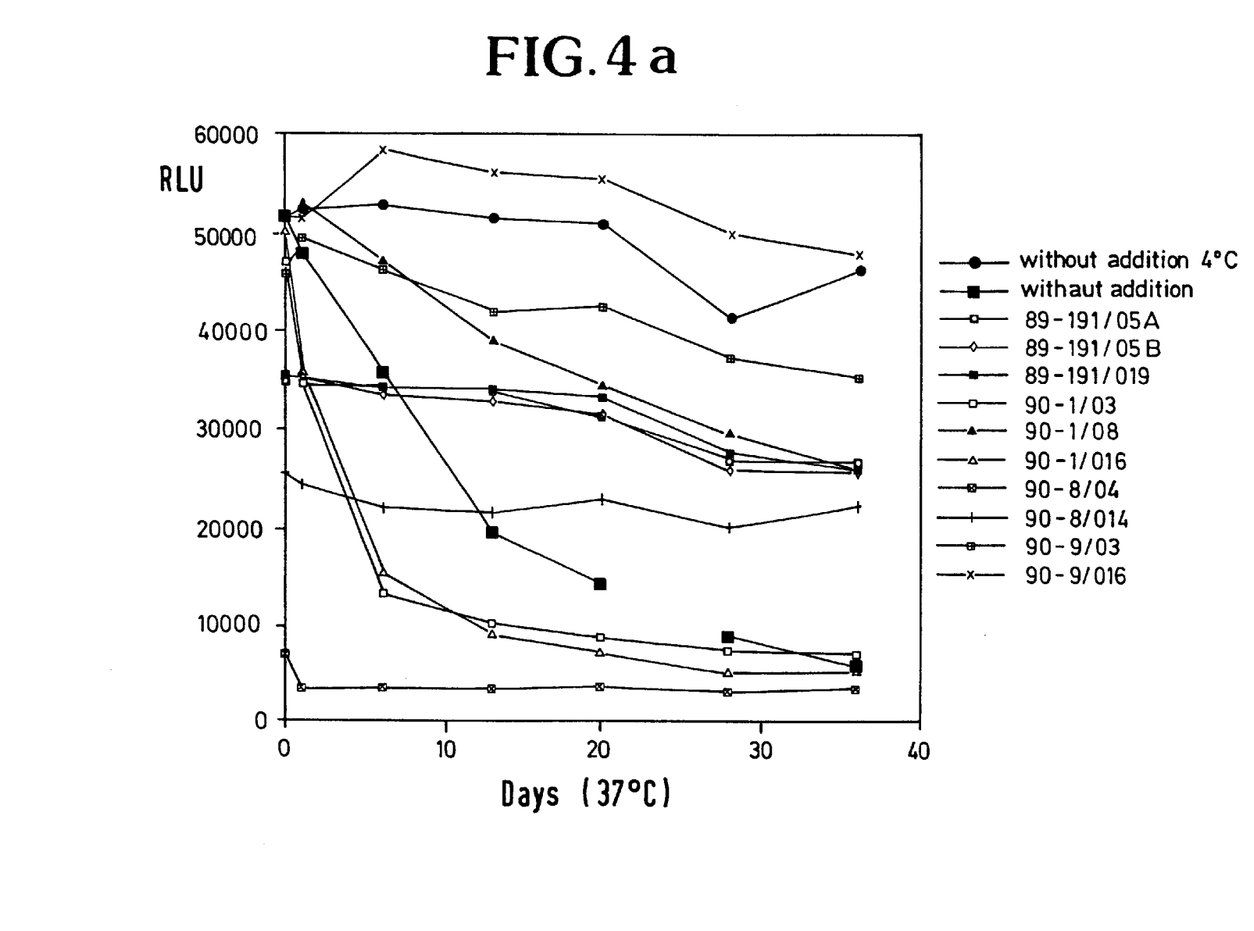
FIG. 4a: Different stabilizing effects of various anti-label antibodies.
Figure 4B:
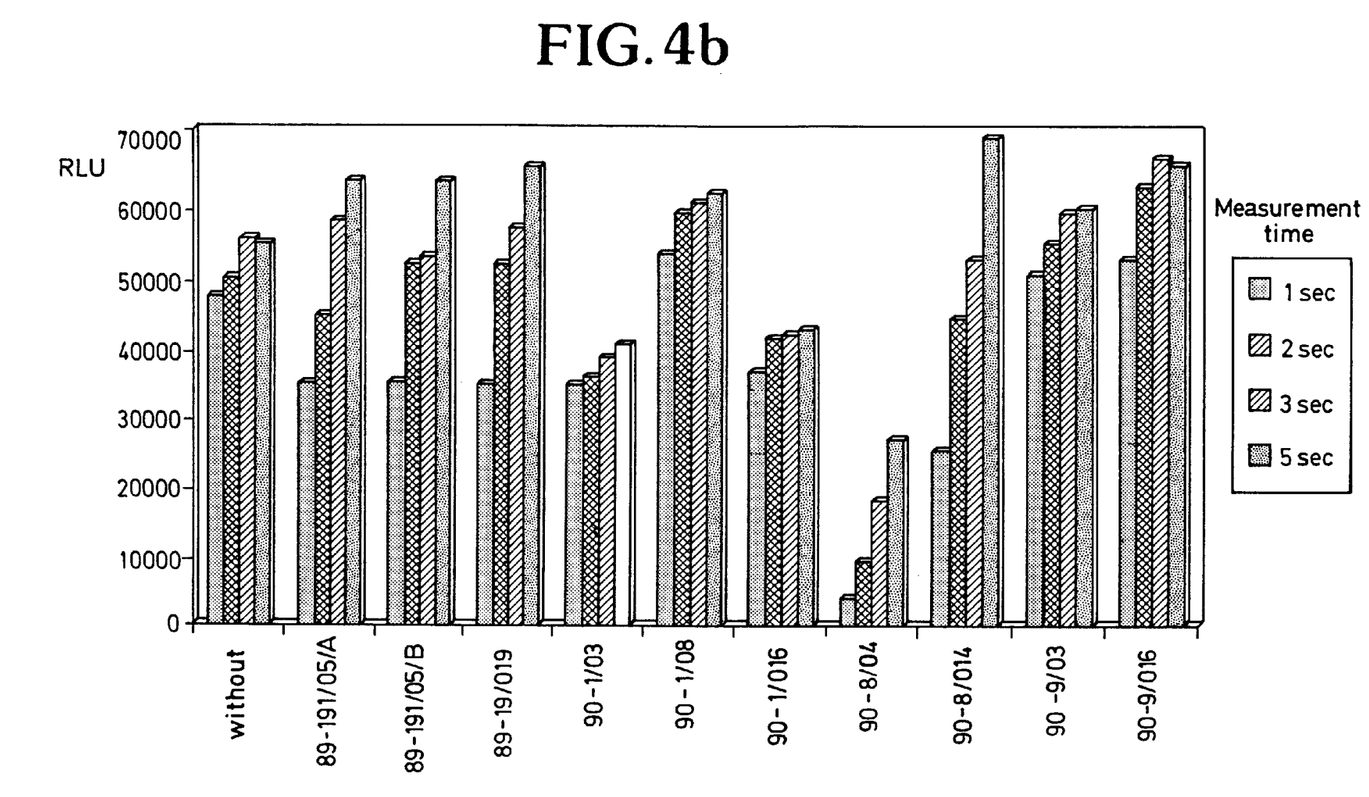
FIG. 4b: Light yields from an anti-PSA tracer as a function of the monoclonal anti-label antibody added.

Some of the investigated anti-label antibodies showed very different behaviors in respect of their ability to stabilize tracers (FIG. 4a) and with regard to the kinetics of light emission. FIG. 4b shows the light yield from the various anti-label antibodies as a function of the measurement time.

The hybridoma detailed below has been deposited at the DSM in Braunschweig. The name of the antibody produced by this hybridoma corresponds to that of the hybridoma.

| Hybridoma | DSM Deposit No. | Date of deposit |
|---|---|---|
| BW 90-342-9-016 | 2183 | 21.07.94 |

We claim:

1. A method for stabilizing hydrolysis-sensitive molecules or hydrolysis-sensitive molecular moieties in aqueous solution, which comprises adding to the aqueous molecule or molecular moiety solution antibodies directed against the molecules or molecular moieties.

2. The method as claimed in claim 1, wherein the hydrolysis-sensitive molecule or the hydrolysis-sensitive molecular moiety is a label used in immunological detection methods.

3. The method as claimed in claim 2, wherein the label is a group capable of luminescence, fluorescence, phosphorescence, chemiluminesence, bioluminescence, absorption or electroluminescence.

4. The method as claimed in claim 3, wherein the label is an acridinium ester, an acridiniumacylsulfonamide a luninol, an isoluminol or derivatives thereof, a dioxetane, a luciferin, an oxalic ester or an oxalic acid amide.

5. The method as claimed in claim 1, wherein the antibody directed against the molecule, the molecular moiety or the label is a monoclonal antibody, a polyclonal antibody, a chimeric antibody, a semi-synthetic antibody, an antibody fragment or a chemically modified antibody antibody or a chemically modified antibody fragment.

6. A kit comprising:
   complex comprising
   (a) a hydrolysis-sensitive molecule or a hydrolysis-sensitive molecular moiety bound to
   (b) a stabilizing antibody directed against said hydrolysis-sensitive molecule or hydrolysis-sensitive molecular moiety.

7. A kit as claimed in claim 6, wherein the molecular moiety to be stabilized is a label.

8. A kit as claimed in claim 7, where the kit is used in an immunological detection method.

9. A kit a claimed in claim 8, wherein the immunological detection method is a competitive immunological detection method comprising an analyte derivative and an antibody, where either the analyte derivative or the antibody has a label, and an antibody directed against the label.

10. A kit as claimed in claim 8, wherein the immunological detection method is a sandwich assay comprising two antibodies which are directed against the analyte and which bind to different epitopes of the analyte, and one of the antibodies has a label, and an antibody directed against the label.

11. A kit as claimed in claim 6, wherein the antibody directed against the molecule, the molecular moiety or the label is a monoclonal antibody, a polyclonal antibody, a chimeric antibody, a semi-synthetic antibody, an antibody fragment or a chemically modified antibody or a chemically modified antibody fragment.

12. A kit for the immunological detection of an analyte comprising:

(a) an analyte-specific antibody;
(b) a label, which is not the analyte, comprising a hydrolysis-sensitive molecule or a hydrolysis-sensitive molecular moiety; and
(c) a stabilizing antibody directed against the hydrolysis-sensitive molecule or a hydrolysis-sensitive molecular moiety,
wherein the stabilizing antibody binds to the hydrolysis-sensitive molecule or hydrolysis-sensitive molecular moiety prior to the binding of the analyte-specific antibody to the analyte.

13. A kit as claimed in claim 12, wherein the analyte is detected using a competitive immunological detection method further comprising an analyte derivative, wherein the label is bound to either the analyte derivative or the antibody.

14. A kit as claimed in claim 12, wherein the analyte is detected using a sandwich assay comprising two antibodies which are directed against the analyte and which bind to different epitopes of the analyte, wherein the label is bound to one of the two antibodies.

15. A kit as claimed in claim 12, wherein the label is a group capable of luminescence, fluorescence, phosphorescence, chemiluminescence, bioluminescence, absorption or electroluminescence.

16. A kit as claimed in claim 12, wherein the label is an acridinium ester, an acridinium-acylsulfonamide, a luminol, an isoluminol or derivatives thereof, a dioxetane, a luciferin, an oxalic ester or an oxalic acid amide.

17. A kit as claimed in claim 12, wherein the stabilizing antibody is a monoclonal antibody, a polyclonal antibody, a chimeric anti-body, a semi-synthetic antibody, an antibody fragment or a chemically modified antibody or a chemically modified antibody fragment.

* * * * *

UNITED STATES PATENT AND TRADEMARK OFFICE
CERTIFICATE OF CORRECTION

PATENT NO.  : 6,010,868
DATED       : January 4, 2000
INVENTOR    : Stephan Neuenhofer et al.

It is certified that error appears in the above-identified patent and that said Letters Patent is hereby corrected as shown below:

In Claim 4, column 6, line 29, after "acridiniumacylsulfonamide", insert --,--.

In Claim 6, column 6, line 39, before "complex", insert --a--.

In Claim 9, column 6, line 49, "kit a" should read --kit as--.

Signed and Sealed this

Sixth Day of March, 2001

Attest:

NICHOLAS P. GODICI

*Attesting Officer*     *Acting Director of the United States Patent and Trademark Office*